United States Patent [19]
Nagata et al.

[11] Patent Number: 6,002,015
[45] Date of Patent: Dec. 14, 1999

[54] METHOD OF PRODUCING 1,2,4-TRIAZOLE

[75] Inventors: Nobuhiro Nagata; Chiharu Nishizawa, both of Mie-ken; Toshikiyo Kurai, Tokyo, all of Japan

[73] Assignee: Mitsubishi Gas Chemical Company, Inc., Tokyo, Japan

[21] Appl. No.: 09/305,450

[22] Filed: May 6, 1999

[30] Foreign Application Priority Data

May 12, 1998 [JP] Japan ................................ 10-128997

[51] Int. Cl.$^6$ .................................................. C07D 249/08
[52] U.S. Cl. ....................................... 548/269.2; 548/262.2
[58] Field of Search ............................................ 548/269.2

[56] References Cited

U.S. PATENT DOCUMENTS

| | | | |
|---|---|---|---|
| 4,267,347 | 5/1981 | Petree et al. | 548/262 |
| 4,390,704 | 6/1983 | Beer | 548/262 |
| 4,490,539 | 12/1984 | Besan | 548/262 |

FOREIGN PATENT DOCUMENTS 56-95177  8/1981  Japan .

*Primary Examiner*—Patricia L. Morris
*Attorney, Agent, or Firm*—Antonelli, Terry, Stout & Kraus, LLP

[57] ABSTRACT

A method of producing 1,2,4-triazole, comprising a step of subjecting a ketazine, water and formamide to a cyclization reaction. The ketazine and water are added simultaneously to formamide kept at a cyclization temperature. Then, ketone by-produced during the cyclization reaction is distilled off while maintaining the reaction mixture at a cyclization temperature to complete the cyclization reaction, thereby obtaining 1,2,4-triazole. The use of the ketazine in place of hydrazine makes the energy-consuming hydrolysis step in the conventional hydrazine production unnecessary. Therefore, the method of the invention is advantageous over the known methods in energy consumption and production cost.

12 Claims, No Drawings

METHOD OF PRODUCING 1,2,4-TRIAZOLE

BACKGROUND OF THE INVENTION

The present invention relates to a method of producing 1,2,4-triazole which is a useful compound having numerous applications such as a starting material for synthesizing agricultural chemicals.

To date, various methods have been proposed for synthesizing 1,2,4-triazole. In all the conventionally known methods, hydrazine is used as the starting material as disclosed in Japanese Patent Application Laid-Open No. 56-95177, and no method utilizing a ketazine, an intermediate of hydrazine production, has been reported.

The ketazine is an intermediate of industrial hydrazine production, and hydrazine is produced by hydrolysis of the ketazine. A substantial portion of energy required in the hydrazine production is consumed during the hydrolysis of the ketazine to result in increased cost of producing hydrazine. This in turn increases the production cost of 1,2,4-triazole.

SUMMARY OF THE INVENTION

Accordingly, an object of the present invention is to provide a method of producing 1,2,4-triazole with a low cost without reducing the yield thereof.

In view of the above object, the inventors have extensively studied synthesis of 1,2,4-triazole using a ketazine as the starting material in place of hydrazine. As a result thereof, the inventors have found that 1,2,4-triazole is easily synthesized by conducting the cyclization reaction while gradually adding a ketazine and water to formamide kept at a cyclization temperature, and distilling off ketone formed during the cyclization reaction. Thus, the present invention provides a method of producing 1,2,4-triazole, comprising a step of subjecting a ketazine, water and formamide to cyclization reaction.

DETAILED DESCRIPTION OF THE INVENTION

The ketazine referred to in the present invention is an aliphatic ketazine having a total carbon number of 3–13, such as a dialkyl ketazine, a cycloalkyl ketazine and a cycloalkanone azine. Specific examples of the ketazine may include acetone azine, methyl ethyl ketazine, methyl isobutyl ketazine, cyclohexanone azine, etc. Of the above ketazines, acetone azine and methyl ethyl ketazine used in the industrial production of hydrazine are preferable because they are economical due to their easy availability and easy handling ability.

In the method of the present invention, it is preferable to add the ketazine and water simultaneously to formamide kept at a cyclization temperature under stirring. The simultaneous addition of the ketazine and water may be accomplished by adding both as a mixture or individually at a time.

The amounts of formamide and water to be used are not specifically limited so long as they are used stoichiometrically or more with respect to the ketazine. In view of industrial economics, the upper limits of the amounts of formamide and water are preferred to be as small as possible. Thus, the amount of formamide to be used is preferably 10 times or less, more preferably 5 times or less by mole based on the ketazine, and preferably 5 times or less, more preferably 3 times or less by mole for water based on the ketazine.

The cyclization temperature is 100–210° C., preferably 150–210° C. Although the cyclization is generally conducted under ordinary pressure, it may be conducted under reduced pressure or increased pressure. The rate of addition of the ketazine and water depends on the cyclization temperature, reacting weight, shape and size of a reaction apparatus, etc. In addition, to efficiently proceed and complete the cyclization, the temperature of the reaction mixture is needed to be kept within the above cyclization temperature range and ketone formed during the cyclization reaction should be distilled off, thereby shortening the residence time of the ketone in the reaction system. To meet these requirements, the ketazine and water are preferably added to formamide over about 3 to 15 hours.

After completing the addition of the ketazine and water, it is preferred to further keep the reaction mixture within the cyclization temperature range under stirring for 1 to 10 hours while distilling off the by-produced ketone to ensure the completion of the cyclization. Then, the remaining water and formamide are removed from the reaction mixture, and finally, 1,2,4-triazole is isolated in a known manner such as distillation under reduced pressure and recrystallization.

As described above, in the method of the present invention, 1,2,4-triazole is easily synthesized from ketazine, water and formamide without using hydrazine. Since the energy-consuming step of hydrolyzing a ketazine into hydrazine inevitable in the conventional hydrazine production can be eliminated, the present invention provides an energy-saving overall method of producing 1,2,4-triazole. In addition, ketone by-produced in the method of the invention is very volatile and easy to distill off as compared with by-products in the conventional method using hydrazine. This ensures a high yield and purity of 1,2,4-triazole without a purification step, and enhances the advantage of the present invention in energy consumption over the conventional methods.

PREFERRED EMBODIMENTS OF THE INVENTION

The present invention will be explained in more detail by reference to the following example which should not be construed to limit the scope of the present invention.

EXAMPLE 1

Into a four-necked 500 ml flack equipped with a stirrer, a condenser, a dropping funnel and a thermometer, were placed 225 g (5 moles) of formamide, which were then heated to 170° C. under stirring. A mixture of 140 g (1 mole) of methyl ethyl ketazine and 54 g (3 moles) of water was added dropwise from the dropping funnel under stirring over 5 hours while distilling off the by-produced ketone by maintaining the resultant mixture at 170° C. After completing the dropping, the mixture was further maintained at 170–180° C. for 3 hours while distilling off the by-produced ketone. The above operation was conducted under ordinary pressure. As a result of gas chromatographic analysis on the reaction mixture, it was found that 1,2,4-triazole was produced in an amount of 61 g, corresponding to 88% yield based on methyl ethyl ketazine.

What is claimed is:

1. A method of producing 1,2,4-triazole, comprising a step of subjecting a ketazine, water and formamide to a cyclization reaction.

2. The method according to claim 1, wherein said cyclization reaction is carried out while distilling off ketone.

3. The method according to claim 1, wherein said ketazine is acetone azine, methyl ethyl ketazine, methyl isobutyl ketazine or cyclohexanone azine.

4. The method according to claim 1, wherein said cyclization reaction is carried out at 100–210° C.

5. The method according to claim 1, wherein said cyclization reaction is carried out under ordinary pressure.

6. A method of producing 1,2,4-triazole by subjecting a mixture of ketazine, water and formamide to a cyclization reaction, comprising the steps of:

adding a ketazine and water simultaneously to formamide kept at a cyclization temperature while distilling off by-produced ketone under stirring; and continuing the stirring at a cyclization temperature while distilling off by-produced ketone to complete said cyclization reaction.

7. The method of producing 1,2,4-triazole according to claim 6, wherein said ketazine is acetone azine, methyl ethyl ketazine, methyl isobutyl ketazine or cyclohexanone azine.

8. The method of producing 1,2,4-triazole according to claim 6, wherein said cyclization temperature is 100–210° C.

9. The method of producing 1,2,4-triazole according to claim 6, wherein the ketazine and water are added to formamide over a period of 3 to 15 hours.

10. The method of producing 1,2,4-triazole according to claim 6, wherein an amount of formamide is a stoichiometric amount or more and 10 times or less by mole with respect to the ketazine.

11. The method of producing 1,2,4-triazole according to claim 6, wherein an amount of water is a stoichiometric amount or more and 5 times or less by mole with respect to the ketazine.

12. The method of producing 1,2,4-triazole according to claim 6, wherein said steps are carried out under ordinary pressure.

* * * * *